(12) United States Patent
Kecskemethy et al.

(10) Patent No.: US 11,106,950 B2
(45) Date of Patent: Aug. 31, 2021

(54) MULTI-MODAL MEDICAL IMAGE PROCESSING

(71) Applicant: KHEIRON MEDICAL TECHNOLOGIES LTD, London (GB)

(72) Inventors: Peter Kecskemethy, London (GB); Tobias Rijken, London (GB)

(73) Assignee: KHEIRON MEDICAL TECHNOLOGIES LTD, London (GB)

( * ) Notice: Subject to any disclaimer, the term of this patent is extended or adjusted under 35 U.S.C. 154(b) by 38 days.

(21) Appl. No.: 16/330,257

(22) PCT Filed: Sep. 5, 2017

(86) PCT No.: PCT/GB2017/052583
§ 371 (c)(1),
(2) Date: Mar. 4, 2019

(87) PCT Pub. No.: WO2018/042211
PCT Pub. Date: Mar. 8, 2018

(65) Prior Publication Data
US 2019/0197366 A1 Jun. 27, 2019

(30) Foreign Application Priority Data
Sep. 5, 2016 (GB) .................................... 1615051

(51) Int. Cl.
*G06K 9/62* (2006.01)
*G06T 7/00* (2017.01)
(Continued)

(52) U.S. Cl.
CPC ......... *G06K 9/6289* (2013.01); *G06K 9/6228* (2013.01); *G06K 9/6257* (2013.01);
(Continued)

(58) Field of Classification Search
CPC .............................. G06K 9/3233; G16H 30/40
(Continued)

(56) References Cited

U.S. PATENT DOCUMENTS

2008/0292194 A1* 11/2008 Schmidt .................... G06T 7/11
382/217
2011/0301447 A1* 12/2011 Park ...................... G06T 7/0016
600/407
(Continued)

FOREIGN PATENT DOCUMENTS

| WO | 2017122785 A1 | 7/2017 |
| WO | 2018042211 A1 | 3/2018 |

OTHER PUBLICATIONS

International Search Report and Written Opinion received for PCT Application No. PCT/GB2017/052583. dated Jan. 30, 2018. 16 pages.

(Continued)

*Primary Examiner* — Kiet M Doan
(74) *Attorney, Agent, or Firm* — Finch & Maloney PLLC (57) ABSTRACT

The present invention relates to the identification of regions of interest in medical images. More particularly, the present invention relates to the identification of regions of interest in medical images based on encoding and/or classification methods trained on multiple types of medical imaging data. Aspects and/or embodiments seek to provide a method for training an encoder and/or classifier based on multimodal data inputs in order to classify regions of interest in medical images based on a single modality of data input source.

19 Claims, 5 Drawing Sheets

(51) Int. Cl.
　　　*G16H 30/40* 　　　(2018.01)
　　　*G06N 3/08* 　　　(2006.01)

(52) U.S. Cl.
　　　CPC ......... *G06K 9/6259* (2013.01); *G06K 9/6269* (2013.01); *G06K 9/6282* (2013.01); *G06N 3/08* (2013.01); *G06T 7/0012* (2013.01); *G16H 30/40* (2018.01); *G06K 2209/05* (2013.01); *G06T 2207/10081* (2013.01); *G06T 2207/10088* (2013.01); *G06T 2207/10116* (2013.01); *G06T 2207/10132* (2013.01); *G06T 2207/20081* (2013.01); *G06T 2207/20084* (2013.01); *G06T 2207/30068* (2013.01)

(58) Field of Classification Search
　　　USPC ..... 382/132, 131, 133, 130, 128, 159; 704/9
　　　See application file for complete search history.

(56) References Cited

U.S. PATENT DOCUMENTS

| | | | |
|---|---|---|---|
| 2015/0016702 A1* | 1/2015 | Huizenga | C23F 11/08 382/131 |
| 2016/0048741 A1* | 2/2016 | Nguyen | G06K 9/00624 382/159 |
| 2016/0093048 A1* | 3/2016 | Cheng | G06K 9/6289 382/131 |
| 2017/0105706 A1* | 4/2017 | Berger | A61B 8/54 |
| 2018/0039884 A1* | 2/2018 | Dalton | G06N 3/063 |

OTHER PUBLICATIONS

Hieung-IL, et al., "Latent feature representation with stacked auto-encoder for AD/MCI diagnosis," Brain Structure and Function, vol. 220, No. 2, Mar. 2015. 40 pages.

Liu, et al., "Multi-Modal Neuroimaging Feature Learning for Multi-Class Diagnosis of Alzheimer's Disease," IEEE Transactions on Biomedical Engineering, vol. 62 No. 4, Apr. 2015. 23 pages.

Makantasis, et al., "Deep Supervised Learning for Hyperspectral data classification through convolutional neural networks," IEEE, IGARSS 2015. pp. 4959-4962.

EPO Office Action received for EP Application No. 17767875.2, dated Feb. 13, 2020. 10 pages.

Mohammad, et al., "HeMIS: Hetero-Modal Image Segmentation," arXiv: 1607.05194v1 [cs.CV], Jul. 18, 2016. 11 pages.

Rastegar, et al., "MDL-CW: A Multimodal Deep Learning Framework with CrossWeights," 2016 IEEE Conference on Computer Vision and Pattern Recognition. pp. 2601-2609.

* cited by examiner

MULTI-MODAL MEDICAL IMAGE PROCESSING

FIELD

The present invention relates to the identification of regions of interest in medical images. More particularly, the present invention relates to the identification of regions of interest in medical images based on encoding and/or classification methods trained on multiple types of medical imaging data.

BACKGROUND

Computer-aided diagnosis (also referred to as CAD) is a technology that has been developed and used for the last 40 years by medical professionals to assist in the interpretation of medical images generated using techniques such as magnetic resonance imaging, x-ray imaging and ultrasound imaging.

Medical imaging techniques such as these produce a large amount of image data, which typically is processed manually by a medical professional, such as a radiologist, and, specifically, is analysed or evaluated by that medical professional in relation to the diagnosis being determined. Typical diagnoses, for example, relate to cancer screening and detection, such as in mammography.

Computer-aided diagnosis can be used with a medical imaging technique to process the image data produced using the medical imaging technique in order to highlight conspicuous regions in each image that might indicate an area of the image of interest to one or more medical professionals, for example a radiologist.

Computer-aided diagnosis is almost never used as a substitute for the opinion of a medical professional as it has not yet reached a level of reliability that medical professionals consider to be acceptable.

Further, some medical image data, such as x-ray image data, is not always the optimal data to achieve a certain diagnosis due to a lack of resolution or clarity in the image(s) obtained. As such, further data or tests need to be performed by the medical professional or other medical professionals to confirm any preliminary diagnosis on the basis of the immediately-available image data.

SUMMARY OF INVENTION

Aspects and/or embodiments seek to provide a method for training an encoder and/or classifier based on multimodal data inputs in order to classify regions of interest in medical images based on a single modality of data input source.

According to a first aspect, there is provided a method for automatically identifying regions of interest in medical or clinical image data, the method comprising the steps of; receiving unlabelled input data, the input data comprising data from one of a plurality of modalities of data; encoding the unlabelled input data using a trained encoder; determining a joint representation using a trained joint representation module; and generating labelled data for the input data by using the joint representation as an input for a trained classifier.

In this way, the method does not need to rely on hand-engineered features to obtain a joint representation of any input data. The present method automatically determines a joint representation using a number of pre-trained components.

Optionally, the encoder, the joint representation module and the classifier are trained with input training data comprising a plurality of modalities. During run-time (or test-time), the method may only receive one input modality. In order to improve the accuracy of identifying regions of interest in medical or clinical data, the pre-trained components are trained using a plurality of input modalities that can be used to determine the joint representation when only one input is received.

Optionally, one or more modalities of input data is provided. In some cases, more than one type of medical image can be used as inputs.

Optionally, the input data comprises one or more of: a mammography; an X-ray; a computerised tomography (CT) scan; a magnetic resonance imaging (MRI) data; histology data; mammography data; genetic sequence data and/or an ultrasound data.

Optionally, the joint representation module is trained using one or more outputs received from the one or more trained encoders.

Optionally, the joint representation module receives the encoded data as three-dimensional tensors of floating point numbers. Optionally, the joint representation is in the form of a vector.

Optimally, generating labelled data further comprises generating an indication of one or more regions of interest in the unlabelled input data.

Optionally, the number of modalities of unlabelled input data is one fewer than the number of modalities of input training data used to train the encoder, the joint representation module and the classifier. In this way the trained components will always have an additional modality of data to assist input data.

According to a second aspect, there is provided a method of training a classifier for medical or clinical data, comprising the steps of: receiving unlabelled input data from a pre-labelled data set, the input data comprising data from a plurality of modalities; encoding the unlabelled input data from a plurality of modalities to form a joint representation; performing classification using an adaptable classification algorithm on the joint representation to generate labelled data from the joint representation; comparing pre-labelled data from the pre-labelled data set to the labelled data and outputting comparison data; adjusting the adaptable classification algorithm in response to the comparison data; and repeating the steps of the method until the comparison data has reached a pre-determined threshold indicating that no further adjustments need to be made to the adaptable classification algorithm.

Optionally, the step of encoding the unlabelled input data from a plurality of modalities to form a joint representation is performed by a plurality of connected and/or paired encoders.

By training a classifier using at least two sources of data, a trained encoder pairing and joint representation can be generated for use in classifying medical or clinical data, for example to identify regions of interest.

Optionally, the input data comprises data from a plurality of sources. Optionally, two modalities of input data are received. Optionally, the unlabelled input data is in the form of one or more medical images. Optionally, the unlabelled input data is in the form of a plurality of medical images. Optionally, the plurality of medical images is related. Optionally, the input data comprises one or more of: a mammography; an X-ray; a computerised tomography (CT)

scan; a magnetic resonance imaging (MRI) scan; and/or an ultrasound scan. Optionally, the medical image is in the form of a DICOM file.

By providing input data from a plurality of sources and/or modalities, such as medical data including for example mammography; X-ray; CT; MRI; and/or ultrasound data, which can be in format of a DICOM file, the training of a classifier, encoder(s) and a joint representation can be performed using this data. If the plurality of medical images is related, for example if they all relate to a specific type of cancerous growth, then a more robust training for the classifier, encoder(s) and joint representation can be performed.

Optionally, the step of encoding the unlabelled input data from a plurality of modalities to form a joint representation is performed separately for each modality.

Producing a joint representation from a plurality of different modalities may require and/or benefit from the use of a specific encoder which has been trained for that modality.

Optionally, the adaptable classification algorithm comprises a machine learning algorithm.

By providing a machine learning algorithm, errors made using the method disclosed herein can be learned from in the future, thereby reducing the number of errors liable to be made in the future.

Optionally, the adaptable classification algorithm comprises a Support Vector Machine (SVM), Multilayer Perceptron, and/or random forest.

Using a classifier that can be trained using backpropagation, for example a multilayer perceptron, allows the parameters of the encoder model to be fine-tuned while the classifier is being trained. SVMs can perform well even on unseen data, by providing a level of robustness and generalisation power. Random forest arrangements can provide faster training speeds, and facilitate feature selection.

According to a third aspect, there is provided a method of classifying data for medical or clinical purposes, comprising the steps of: receiving unlabelled input data; the input data comprising data from one of a plurality of modalities of data; encoding the unlabelled input data into a trained joint representation using a trained encoder; and performing classification using an learned classification algorithm on the trained joint representation to generate labelled data from the trained joint representation. Optionally, one modality of input data is provided.

By training a classifier using two sources of data, a trained encoder and joint representation can be generated for use to classify medical or clinical data, for example to identify regions of interest. Such a classification may be performed using only a single modality, as only a single modality may be present when required, for example if a patient has just received an X-ray but no further examination has been carried out. However as described earlier, the method of training and hence classification can derive benefit from other modalities even when immediately absent.

Optionally, the step of performing classification further comprises generating an indication of one or more regions of interest in the unlabelled data. Optionally, the one or more regions of interest are indicative of a cancerous growth.

By drawing attention to a region of interest, a user can review a portion of a medical image which they may otherwise have neglected. A user may also save time by being able to review non-indicated regions in less detail, and so avoid wasting effort analysing portions of an image in which there is no interest.

Optionally, the number of modalities of unlabelled input data is one fewer than the number of modalities of input data used to train the learned classification algorithm. Optionally, any encoders or decoders used are CNNs, including any of: VGG, and/or AlexNet; and/or RNNs, optionally including bidirectional LSTM with 512 hidden units.

According to a fourth aspect, there is provided an apparatus for training a classifier and/or classifying data for medical or clinical purposes using the respective methods as herein described.

BRIEF DESCRIPTION OF DRAWINGS

Embodiments will now be described, by way of example only and with reference to the accompanying drawings having like-reference numerals, in which.

SPECIFIC DESCRIPTION

Figure 1:
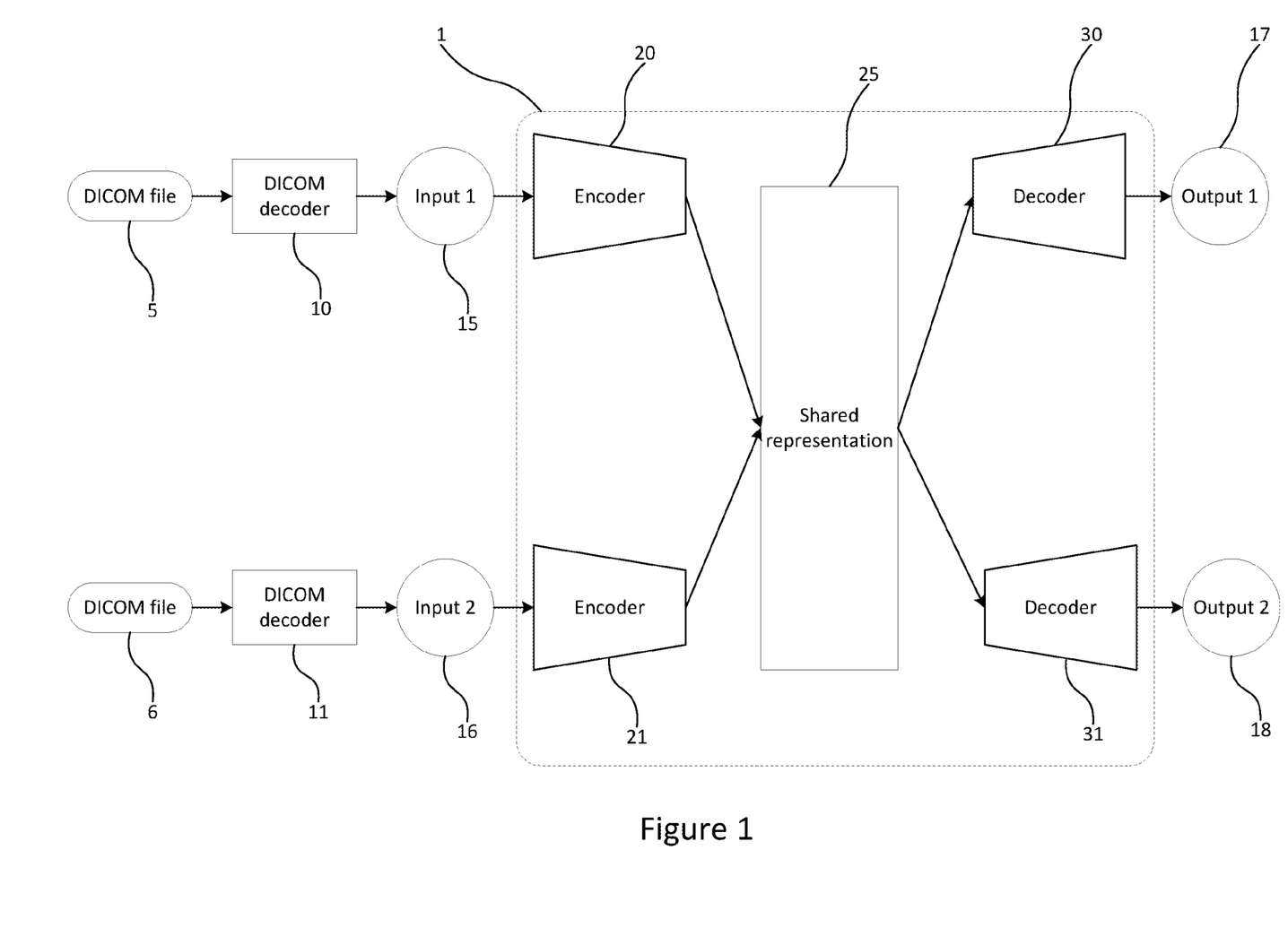
FIG. 1 illustrates a training process for a multimodal neural encoder.

Referring to FIG. 1, a first embodiment will now describe the training of a multimodal neural encoder 1.

In this embodiment, there is provided a method for training a multimodal neural encoder 1 which, in this embodiment, is operable to receive two or more separate Digital Imaging and Communications in Medicine (DICOM) files 5, 6. Each of the DICOM files 5, 6 is input to a DICOM decoder 10, 11. Each of the DICOM files 5, 6 can be from different types of sensor or imaging technique (or "modality"), so from a different source of information. One DICOM file 5, for example, can be from X-ray data, and the other DICOM file 6 can be from histological data. Similarly, any combination of X-ray data, histology data, MRI data, mammography data and genetic sequence data can be used as inputs.

The input data can be of any modality and with any type of dimensionality. As an example, one input may be two-dimensional mammographic image and a second input may be one-dimensional genetic data.

The DICOM decoder 10, 11 reads the corresponding DICOM image 5, 6 and converts it to a lossless Joint Photographic Experts Group (JPEG) image. The JPEG images 15, 16 are read into memory, where they are represented as 3-dimensional tensors of floating point numbers.

These tensors are then fed into a corresponding encoder 20, 21 to obtain a shared representation (sometimes referred to as joint representation) 25. By implementing machine learning techniques, the system automatically learns and creates the most appropriate joint representation. The joint representation 25 can be in the form of a vector (i.e. a 1-dimensional tensor) of a given length. The precise length is arbitrary, but in this embodiment it is usually in the range of 512 to 4000 elements, where each element is a real number. The outputs from each encoder 20, 21 feed into the same joint representation 25. The elements in the joint representation are real numbers connected by weights received from the encoders 20, 21. Thus, the joint representation is created by using a set of weights from multi-modal inputs. Each input has its own set of weights to create the joint representation. For example, consider a scenario with two input modalities. A representation for the first input modality is created as follows:

$$y^{(1)} = f^{(1)}(W^{(1)}x^{(1)} + b^{(1)})$$

where $f^{(1)}$ is a non-linear function, $W^{(1)}$ is a set of weights, $x^{(1)}$ is the input, and $b^{(1)}$ is the bias for the first modality. A representation for the second modality is created as follows:

$$y^{(2)} = f^{(2)}(W^{(2)}x^{(2)} + b^{(2)})$$

where $f^{(2)}$ is a non-linear function, $W^{(2)}$ is a set of weights, $x^{(2)}$ is the input, and $b^{(2)}$ is the bias for the second modality.

Accordingly, the output representation of each encoder is a vector. When there are a plurality of encoders, each serving a different input modality, they may have the same length. For example, for n different inputs:

$$len(y^{(1)}) == len(y^{(2)}) == len(y^{(3)}) == \ldots == len(y^{(n)})$$

These vectors can then be combined into one joint representation of the same length (len) as individual vectors. The vectors can be combined in a number of ways in the neural network. This may be done through:
1. Summation: where the joint representation is a sum of all n vectors;
2. Average pooling: where the average of all n vectors is taken as the joint representation;
3. Max pooling: where the largest value of the n vectors is taken as the joint representation; or
4. Learnt pooling: where a convolution layer with a 1×1 kernel is used to develop a weighted average for each of the n vectors, and the weights in a convolutional layer can be trained.

Learnt pooling can provide more flexibility to develop the best method of combining the individual representations into a joint representation. Moreover, through the training process, the best weighted averages can be set automatically through backpropagation.

Figure 2:
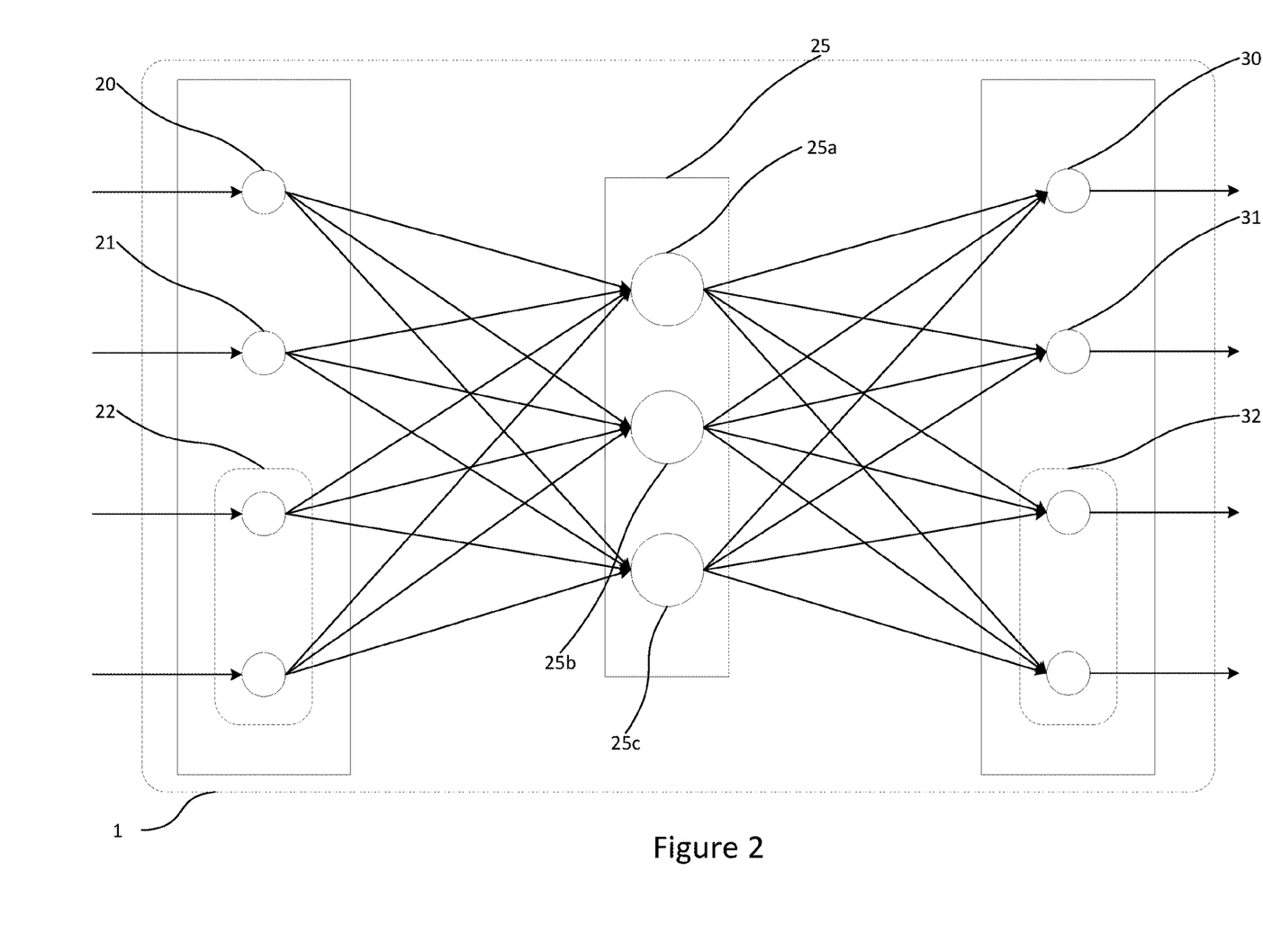
FIG. 2 illustrates a more detailed view of the encoder-decoder architecture.

Referring to FIG. 2, a more detailed version of the multimodal neural encoder 1 will now be described.

The first element 25a in the joint representation will receive input weights from each encoder 20, 21, as does the second element 25b, and the third 25c, and so on for any further elements (not shown). Further encoders 22 (which may include other encoders not shown) may also feed into a common joint representation 25, depending on the number of image modalities being analysed. A greater number of modalities of input can provide a more effective and/or efficient way of training the encoders 20-22. Each output from every encoder is connected to every element in the joint representation. The weights between layers are stored in a matrix. Many CNNs which may be used as part of the multimodal neural encoder 1 have a low-level representation at one end or end layer. The CNNs can therefore comprise a number of convolutional layers followed by a fully connected layer. One or more of the CNNs can be operable to encode a high-dimensional input into a lower dimensional representation. In this embodiment, such a representation is in the form of the joint representation 25, but further comprises multiple encoders sharing the same representation. Each encoder 20-22 is operable to connect to the same fully connected layer. The joint representation 25 is a data structure operable to be fully connected to a layer of each encoder 20-22 and a layer of each decoder 30-32, receiving inputs from all the encoders 20-22, and sending its outputs to all the decoders 30-32.

To produce a useable joint representation 25, a weighted sum is performed over the outputs of any encoders. If there are multiple encoders, as shown in this representation for encoders 20-22, the joint representation is a weighted sum over the outputs of all encoders 20-22. The weights for the joint representation 25 are only updated during training, and remain constant during runtime, as will be described in reference to FIG. 4. During runtime, the algorithm that performs a weight update, which in this embodiment is a backpropagation algorithm, is not run at all. The data provided from the joint representation 25 is then output to one or more decoders. Each decoder 30, 31 then restores the data back into JPEG images 15, 16. Each decoder 30, 31 is suitable to decode at least one modality of input data, including one of the modalities of the original DICOM files 5, 6. If further encoders 22 were used to feed data into the same joint representation 25, then further decoders 32 may be used to restore the data back into JPEG images.

The joint representation 25 is therefore trained using the weights received from each encoder. Further training of the multimodal neural autoencoder 1 can be performed using backpropagation and gradient descent. Backpropagation computes the gradient of the error with respect to the parameters. Gradient descent is then used to update the weights. The error function, or reconstruction criterion, is the mean squared error:

$$E = \frac{1}{2n} \sum_{i=1}^{n} (x_i - y_i)^2$$

where $x_i$ and $y_i$ are pixels in the input and reconstructed image respectively. This training procedure is an unsupervised learning task. Hence, no labelled data is required:

$$D_n = \{(x_0), \ldots, (x_n)\}$$

The multimodal neural autoencoder 1 thereby trains the encoders 20, 21 and the joint representation 25. The decoders 30, 31 do not need to be trained during this process. The training process occurs substantially simultaneously for all components being trained, which is known as an 'end-to-end' process. The autoencoder 1 is operable to encode an input 15, 16 into a lower dimensional joint representation 25, and then reconstruct the input through the decoders 30, 31 into an output 17, 18 which is substantially the same as the input 15, 16 that was given to the encoder. The weights in both the encoders 20, 21 and decoders 30, 31 are trained at the same time, using the backpropagation algorithm.

The weights can be updated by providing an input 15, which then undergoes a 'forward pass' through the process and in doing so is eventually processed into an output 17. If the output 17 does not match an expected output (from a training set), the difference between the two is an error. The error can then be backpropagated through the process, thereby computing the gradient of the loss with respect to each parameter. The weight can then be updated for accuracy by setting the gradient to zero. Therefore, if the output 17 is too different from the input 15, then the algorithm is penalised. As the output is arranged to be the same as the input, and a training set is used, this stage of the process of training the multimodal neural encoder 1 can be performed unsupervised.

Figure 3:
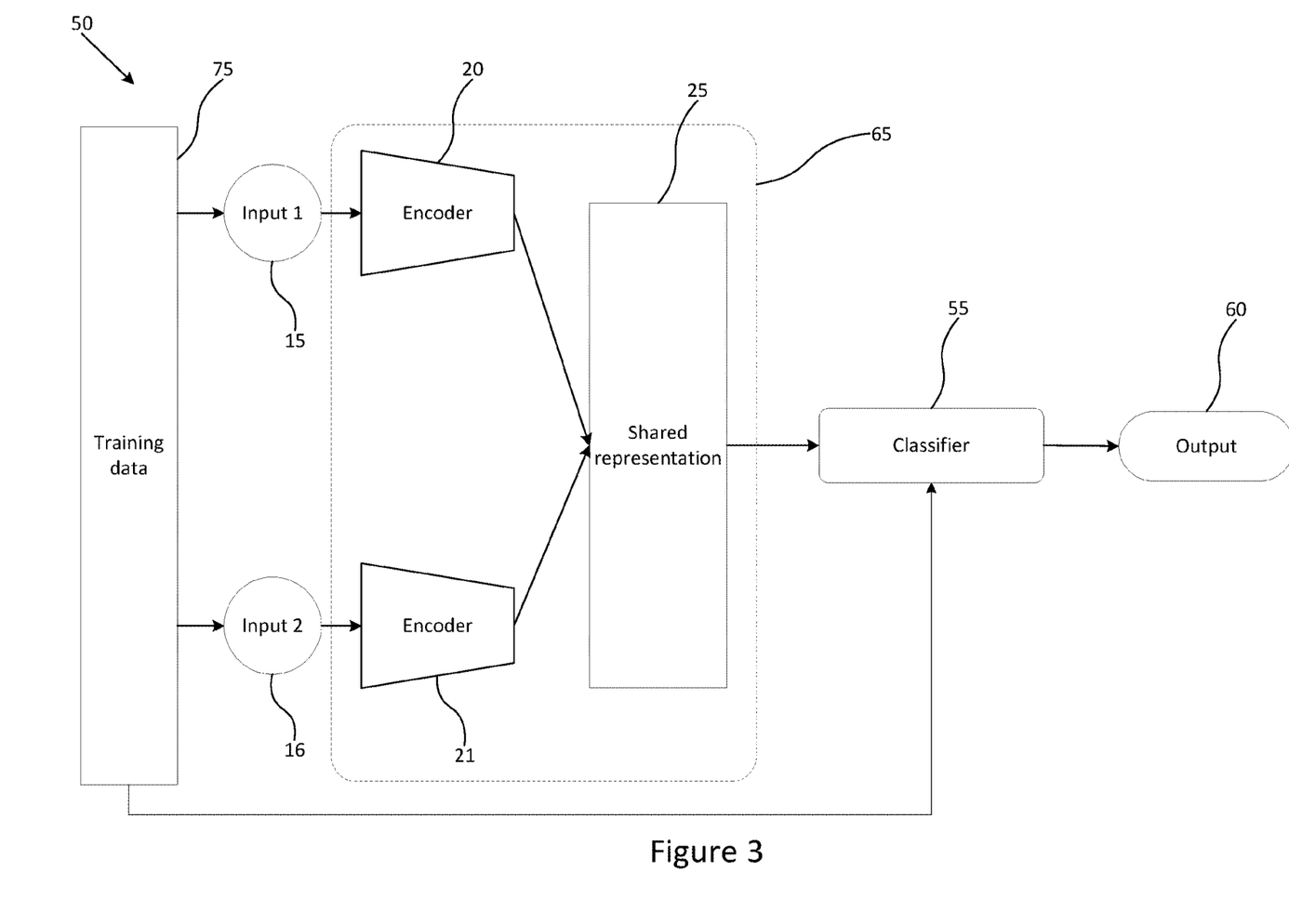
FIG. 3 illustrates a training process for a classifier.

Referring to FIG. 3, the specifics of training a classifier will now be described as follows.

Once the multimodal neural autoencoder 1 has undergone unsupervised pre-training using multiple modalities, a multiple encoder module 65 comprising encoders 20, 21 and the joint representation 25 can serve as input to a classifier 55 as part of the train time 50. The classifier may be in the form of a multilayer perceptron, support vector machine (SVM), or random forest, etc. When using a multilayer perceptron for the classifier, the classifier can be trained by means of backpropagation and gradient descent as well, allowing more accessible fine-tuning of the pre-trained weights from the encoder. This training procedure is a supervised learning task and requires a labelled dataset:

$$D_n = \{(x_0, y_0), \ldots, (x_n, y_n)\}$$

where $x \in \mathbb{R}^d$ is a d-dimensional image and $y \in [0, 1]$ is a label.

The output for this stage of training the classifier is a label of the (image) input, rather than the image itself as before. Therefore, in order to compute an error, if one or more is present, a dataset comprising these labels is required. Such a dataset is provided in the form of training data 75, which has already been classified and provided with relevant labels. Therefore, when the classifier 55 generates a label based on an input provided, the label can be checked with a label known to be correct from the training data 75. As referred to in FIG. 2, any differences between the two labels will be the result of an error and backpropagation can be performed to find and reduce the source of the error.

The type of classifier used, for example SVM, random forest, or multilayer perceptron, can be trained using a separate training algorithm. These algorithms may comprise max-margin optimization, averaging over decision trees, and backpropagation respectively.

Figure 4:
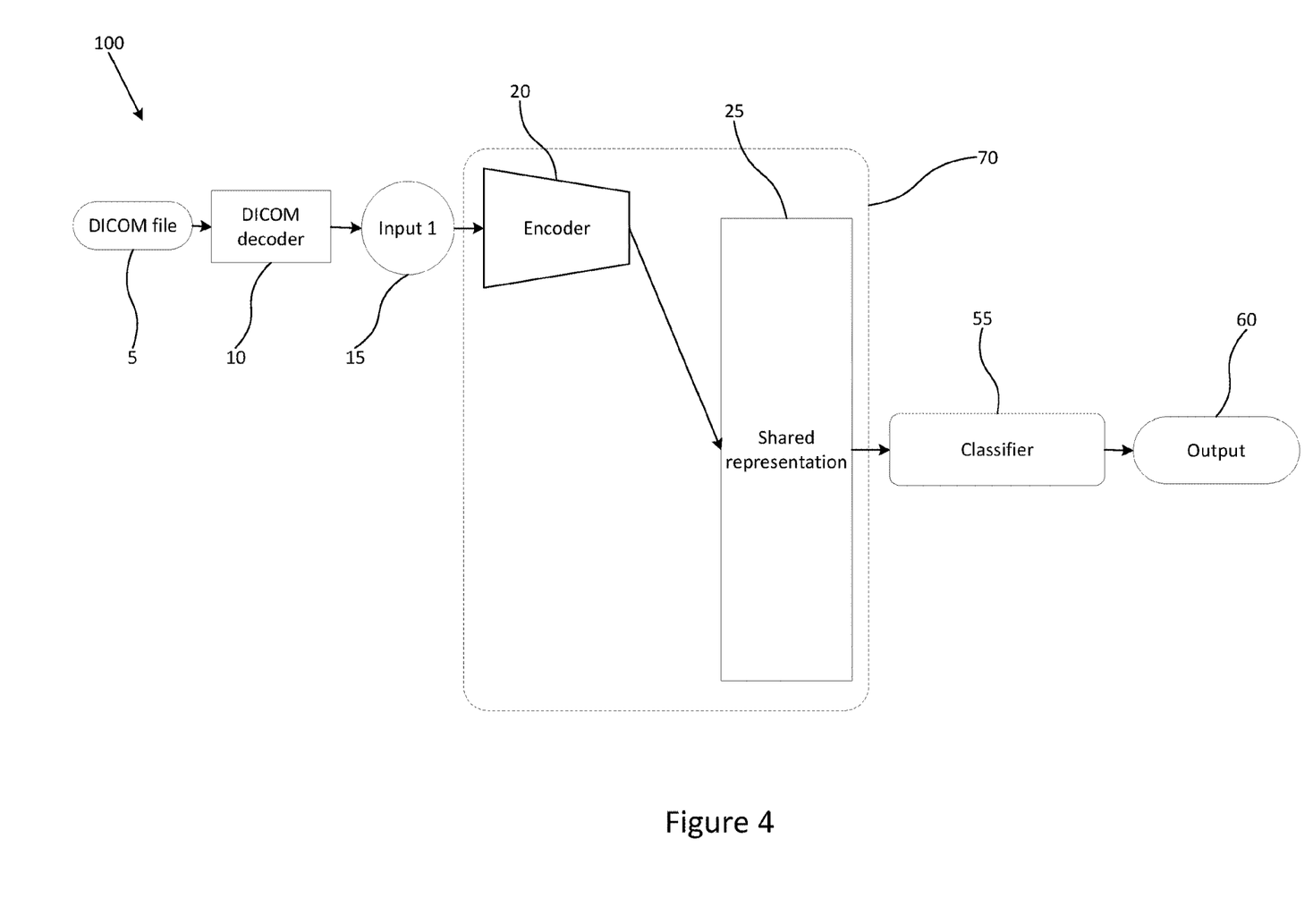
FIG. 4 illustrates the trained classifier in use.

Referring now to FIG. 4, the process of using the trained classifier will now be described in more detail.

FIG. 4 shows the runtime 100 once the classifier is trained using the pre-trained encoder models that correspond to the modalities of which we have labelled data. During runtime 100, the values of the real numbers in the joint representation 25 are different for every data point supplied, but the weights for the joint representation remain constant. In this example, a single input in the form of a DICOM file 5 is fed into a DICOM decoder 10, which, as before, reads the DICOM image and converts it to a lossless JPEG image 15. The JPEG image is then read into memory. There it is represented as a 3-dimensional tensor of floating point numbers. The tensor is fed into the encoder 20 to obtain the joint representation 25. A reduced encoder module 70 is provided, and comprises the encoder 20 and the joint representation 25. The reduced encoder module 70 provides an output which is fed into the classifier 55, whereupon the classifier outputs a prediction. Further training may also be provided during runtime 100, and/or through the use of the reduced encoder module 70.

Figure 5:
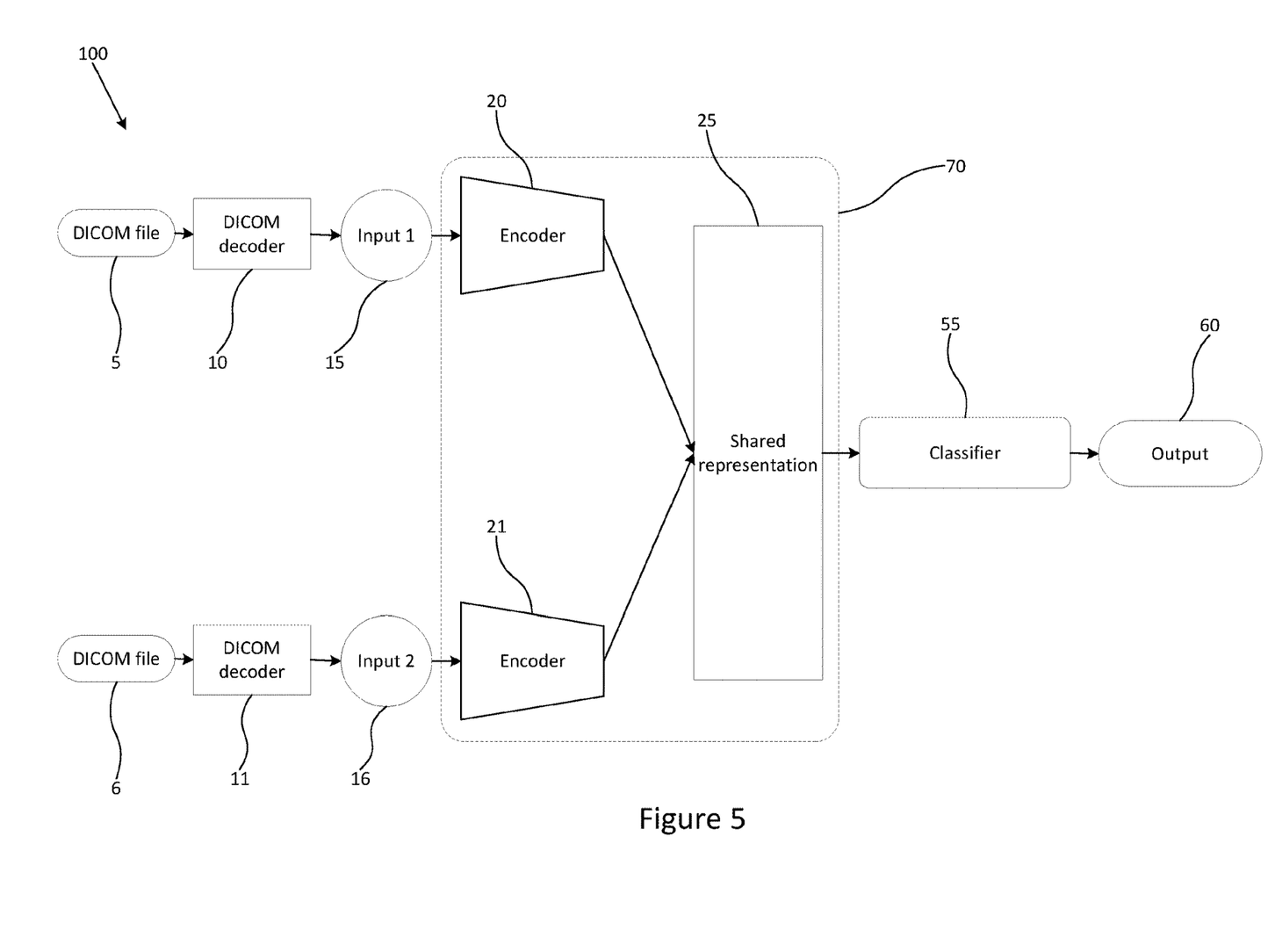
FIG. 5 illustrates a second example of a trained classifier in use.

Further to the illustration of FIG. 4, FIG. 5 shows an example of multiple inputs in the form of DICOM files. In this example, each input may relate to different modalities as described above in the training phase.

There is provided a computer aided diagnostic (CAD) system, operable to identify regions of interest in a medical image. The function that classifies a pathology from a medical image is a non-linear, highly complex function. A convolutional neural network (CNN) can model any such function:

$$y = f(Wx + b)$$

where f is the non-linear function, W is a matrix of weights, x is the input and b is a bias vector.

The matrix of weights is optimized to minimize an error criterion through the use of the multi-phase training, comprising: using an image reconstruction criterion to obtain a trained multimodal neural autoencoder 1 through a joint representation 25; and training a classifier 55 by providing an input which goes through the pre-trained joint representation 25 to obtain the joint representation for both modalities.

The CAD is therefore able to provide an identification of a region of interest in medical images through the use of a joint representation of different modalities, even though only a single modality may be provided at a given moment. For example, if a patient has only received an X-ray, and no further information is accessible, then an analysis of the image can be provided with the benefit of other, absent, modalities. The invention is therefore operable to learn features from multiple modalities (e.g. mammograms and corresponding histology images), but needs only one modality at runtime to perform the analysis. A preferable way to make predictions is from a cell-level histology image. However, when a patient is diagnosed, histological data is typically absent and there is only access to medical imaging data.

The output of the classifier 55 may be in the form of a simple 'yes/no' answer indicating whether or not there is an abnormality in the input 15 received. The CAD may take patches of the input picture and ascertain whether or not there is an abnormality in that individual patch. The CAD may perform such an operation for a grid of pitches covering the whole input, thereby allowing a region of interest to be identified around areas that appear to have such abnormalities.

In this embodiment, specifically two inputs 15, 16 are used to train the multimodal neural encoder 1 and classifier 55. However only a single input is required to then use the trained neural encoder 1 and classifier 55. The output produced can benefit from training gained using further data (e.g. histological data), which is not provided during runtime. A plurality of inputs may be provided in some embodiments, with one or more fewer inputs required to then use the trained neural encoder 1 and classifier 55 to produce an output.

Any system feature as described herein may also be provided as a method feature, and vice versa. As used herein, means plus function features may be expressed alternatively in terms of their corresponding structure.

Any feature in one aspect may be applied to other aspects, in any appropriate combination. In particular, method aspects may be applied to system aspects, and vice versa. Furthermore, any, some and/or all features in one aspect can be applied to any, some and/or all features in any other aspect, in any appropriate combination.

It should also be appreciated that particular combinations of the various features described and defined in any aspects can be implemented and/or supplied and/or used independently.

The invention claimed is:

1. A method for automatically identifying regions of interest in medical or clinical image data, the method comprising:
receiving unlabelled input data at a multimodal neural encoder comprising a trained encoder and a trained joint representation module, the unlabelled input data comprising data from one or more different modalities of unlabelled input data, wherein the one or more different modalities of unlabelled unlabeled input data is one fewer modality than a number of different modalities of input training data used to train both the trained encoder and the trained joint representation module;
encoding the unlabelled input data using the trained encoder;

determining a joint representation from the encoded unlabelled input data using the trained joint representation module; and generating labelled data for the unlabelled input data by using the joint representation as an input for a trained classifier, wherein the trained classifier is trained with the input training data, wherein the trained encoder comprises a different bias for each of the number of different modalities of input training data used to train the trained encoder.

2. The method of claim 1, wherein the trained encoder comprises a different set of weights for each of the number of different modalities of input training data used to train the trained encoder.

3. The method of claim 1, wherein only one modality of unlabelled input data is provided to the multimodal neural encoder.

4. The method of claim 1, wherein the unlabelled input data received by the multimodal neural encoder comprises one or more of: a mammography; an X-ray; a computerised tomography (CT) scan; a magnetic resonance imaging (MRI) data; histology data; mammography data; genetic sequence data; and/or an ultrasound data.

5. The method of claim 1, wherein the trained joint representation module is trained using one or more outputs received from the trained encoder.

6. The method of claim 1, wherein the trained joint representation module receives the encoded unlabelled input data as three-dimensional tensors of floating point numbers.

7. The method of claim 1, wherein the joint representation is in the form of a vector.

8. The method of claim 1, wherein generating labelled data comprises generating an indication of one or more regions of interest in the unlabelled input data.

9. The method of claim 1, wherein encoding the unlabelled input data comprises encoding using a plurality of trained encoders.

10. The method of claim 9, wherein the plurality of trained encoders output a plurality of vectors having a same length used to train the trained joint representation module, each vector of the plurality of vectors representing a different modality of the input training data.

11. The method of claim 1, wherein the trained encoder of the multimodal neural encoder comprises a convolutional neural network.

12. The method of claim 1, wherein the input training data used to train the trained joint representation module comprises image data and non-image data.

13. The method of claim 1, wherein the trained joint representation module of the multimodal neural encoder comprises a learnt pooling operation, and the trained encoder of the multimodal neural encoder comprises a convolutional neural network.

14. A method of classifying data for medical or clinical purposes, comprising:
receiving unlabelled input data at a multimodal neural encoder comprising an encoder and a joint representation module, the unlabelled input data comprising data from one or more different modalities of unlabelled input data, wherein the one or more different modalities of unlabelled input data is one fewer modality than a number of different modalities of input training data used to train both the encoder and the joint representation module;

encoding the unlabelled input data into a joint representation using the encoder and the joint representation module; and performing classification using a classification algorithm on the joint representation to generate labelled data from the joint representation, wherein the classification algorithm is trained with the input training data, wherein the trained encoder comprises a different bias for each of the number of different modalities of input training data used to train the trained encoder.

15. The method of claim 14, wherein only one modality of input data is provided.

16. The method of claim 14, wherein performing classification comprises generating an indication of one or more regions of interest in the unlabelled data.

17. The method of claim 16, wherein the one or more regions of interest are indicative of a cancerous growth.

18. The method of claim 14, wherein encoding the unlabelled input data comprises encoding using a plurality of trained encoders.

19. The method of claim 14, wherein the encoder of the multimodal neural encoder is a convolutional neural network, including any of: VGG neural network, AlexNet neural network, and/or recurrent neural network (RNN), optionally including bidirectional long short-term memory (LSTM) with 512 hidden units.

* * * * *